(12) United States Patent
O'Uchi et al.

(10) Patent No.: US 6,682,718 B1
(45) Date of Patent: Jan. 27, 2004

(54) REMEDIES FOR PERIODONTOSIS

(75) Inventors: Naoto O'Uchi, Itabashi-ku (JP); Takaya Iwai, Tsukuba (JP); Taiji Yoshino, Tsukuba (JP); Hiroyuki Kanoh, Tsukuba (JP); Hiroyuki Motoie, Itabashi-ku (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/130,795

(22) PCT Filed: Nov. 22, 2000

(86) PCT No.: PCT/JP00/08246

§ 371 (c)(1), (2), (4) Date: May 23, 2002

(87) PCT Pub. No.: WO01/37842

PCT Pub. Date: May 31, 2001

(30) Foreign Application Priority Data

Nov. 25, 1999 (JP) ............................................. 11-334885

(51) Int. Cl.$^7$ ............................ A61K 7/16; A61K 31/66
(52) U.S. Cl. ........................ 424/49; 514/108; 514/102
(58) Field of Search ...................... 400/49–58; 514/102, 514/108

(56) References Cited

U.S. PATENT DOCUMENTS 5,041,428 A * 8/1991 Isomura et al.
6,117,856 A * 9/2000 Binderman et al.
6,331,533 B1 * 12/2001 Harvey et al.

FOREIGN PATENT DOCUMENTS

| EP | 325 482 | * | 7/1989 |
| WO | 97 29754 | * | 8/1997 |
| WO | WO 97/29754 A1 | | 8/1997 |
| WO | 2000028954 | * | 5/2000 |

OTHER PUBLICATIONS

O'uchi et al J. Per. Res. 33(4): 196–204 May 1998.*
Adachi et al. J. Dent. Res 73(8): 1478–1486, 1994.*
Okamoto et al HCAPLUS 122:71982, 1995.*
Hirosawa HCAPLUS 125:158294, 1996.*
Hasegawa HCAPLUS 126:272304, 1997.*
Annen et al HCAPLUS 130:457, 1998.*
International Search Report.
Adachi, et al. "Effects of Topical Administration of a Bisphosphonate (Risedronate) on Orthodontic Tooth Movements in Rats." Journal of Dental Research, vol. 73(8), pp/ 1478–1484, Aug., 1994.
O'Uchi, et al. "Inhibitory effects of YM175, a bisphosphonate, on the progression of experimental periodontitis in beagle dogs" Journal of Periodontal Research, vol. 33, pp. 106–204, 1998.
Yukiko Oikawa. "Effects of bisphosphonate (pamidronate) on the osteoclast during the experimental tooth movement". Orthodontic Waves. vol. 57(5), pp. 307–317, 1998.
Masaaki Okamoto, et al. "Effect of new bisphosphonate, YM< 175, on experimental periodontis in hamsters" Journal of Oral Biology, vol. 36, pp. 510–519, 1994.
Weinreb, et al. "Histomorphometrical analysis of the effects of the bisphosphonate alendronate on bone loss caused by experimental periodontitis in monkeys" Journal of Periodontal Research. vol. 29, pp. 35–40, 1994.
Hayato Annen, "Effect of topical administration of a bisphosphonate (YM–175) on experimental tooth movement—induction of apoptosis in osteoclasts—." 1998.

* cited by examiner

*Primary Examiner*—Shep K. Rose
(74) *Attorney, Agent, or Firm*—Sughrue Mion, PLLC

(57) ABSTRACT

The invention relates to an alveolar bone resorption inhibitor for use in topical injection by an alveolar mucosa injection method, which comprises a bisphosphonic acid derivative or a salt thereof as an active ingredient and to an alveolar bone resorption inhibitor for human periodontal tissue topical injection, which comprises a bisphosphonic acid derivative or a salt thereof in a concentration small enough so that local irritation to human periodontal tissues as the administrating site is acceptable but sufficient enough for expressing alveolar bone resorption inhibitory action by topical injection.

7 Claims, 3 Drawing Sheets

REMEDIES FOR PERIODONTOSIS

TECHNICAL FIELD

This invention relates to medicaments, particularly a pharmaceutical composition for periodontitis treatment as periodontal tissue local injection, which comprises a bisphosphonic acid derivative or a salt thereof as an active ingredient.

TECHNICAL BACKGROUND

Periodontitis is a disease in which chronic gingivitis progresses and inflammation is also spread to periodontal tissues other than gingiva, which accompanies progressive destruction of periodontal tissues. Clinically, chronic inflammation of gingiva, bleeding from periodontal pockets, alveolar bone resorption and the like are observed, and it is known that mobility and movement of teeth occur as the destruction advances, finally causing spontaneous loss of a tooth or a necessity of tooth extraction. The treatment of periodontitis includes removal of dental plaque and dental calculus as causal substances, and removal of degenerative, necrosed tissues by root planing and periodontal surgery and the like for the purpose of effecting reattachment of gingiva (Periodontal Therapy (2nd edition), pp. 215–226 (1992), published by Ishiyaku Shuppan). In the drug therapy of periodontitis, tetracycline antibiotics are mainly used with the aim of removing periodontitis-associated bacteria. However, a drug that directly acts upon alveolar bone resorption, which is an important clinical manifestation of periodontitis, does not exist to date, so that a drug having such an action is expected to have usefulness as a novel therapeutic agent for periodontitis.

Bisphosphonate (hereinafter, BP) is a structural analog of pyrophosphoric acid, which is stable in the living body, and has biological actions such as heterotopic calcification inhibitory action, bone resorption inhibitory action and the like. BP has already been used in the clinical field as a therapeutic agent for hypercalcemia accompanied by a malignant tumor, Paget's disease, osteoporosis and the like, and its action on alveolar bone resorption caused by periodontitis is also expected due to its pharmacological actions. An action of BP to inhibit periodontal tissue destruction in rats has been reported (*J. Dent. Res.*, 11, 1430–1433 (1988)), and it has been reported in recent years that alendronate, which is a second generation BP, inhibited alveolar bone destruction in monkey and dog periodontitis models by its oral administration (*J. Periodontol.*, 63, 825–830 (1992), *J. Periodontol.*, 66(3), 211–217 (1995)). Also, it has already been reported that incadronate disodium (chemical name disodium cycloheptylaminomethylenediphosphonate monohydrate; to be referred to as incadronate hereinafter) is a third generation BP having potent bone resorption inhibitory action (Japanese Patent Publication No. 629/1995) and exerts alveolar bone loss inhibitory action in a hamster periodontitis model (*Dentistry Basic Medicine Journal*, 36(5), 510–519 (1994)) and alveolar bone loss inhibitory and attachment level improving actions in a canine periodontitis model, by its subcutaneous or oral administration respectively (*J. Periodont. Res.*, 33, 196–204 (1998)).

In such oral administration, subcutaneous injection, intravenous injection and the like systemic administrations, it is considered that bone resorption inhibitory action is exerted by the transfer of drug effect-inducing amount of BP into an affected part of the alveolar bone, and there is a possibility that BP is simultaneously transferred into other tissues in the same manner, and express bone resorption inhibitory action particularly in systemic bone tissues in the same manner, thus inducing undesirable actions.

On the other hand, attempts have been made to administer BP topically; for example, it has been reported that topical administration of risedronate to the sub-periosteum area adjacent to the first molar and topical administration of pamidronate to sub-mucasa on palate-side are effective in rat molar experimental tooth movement models (*J. Dent. Res.*, 73(8), 1478–1484 (1994); *Orthod. Waves*, 57(5), 307–317 (1998)).

However, there are no reports to date on alveolar bone resorption inhibitors for use in the topical administration of BP, which are clinically usable in human. Actually, since there are differences in the shape, size, stimulation property and the like of periodontal tissues between rats and human, it is difficult to predict suitable topical administration concentration, dose, administration method and the like at human periodontal tissues or their periphery from the above information in rats.

WO 93/11774 discloses a periodontitis-treating agent of alendronate, but its main administration method is a systemic administration by oral administration or intravenous injection. Regarding its topical administration, it is described that it can be directly applied to inflammatory parts of teeth and gingiva, but there are no illustrative disclosures on its dose, administration site and the like, merely suggesting a possibility. What is more, in this method for directly applying it to inflammatory parts of teeth and gingiva, not only transfer rate of BP into alveolar bone is low but also a possibility of orally systemic administration with saliva is suggested, so that its alveolar bone-selective administration cannot be expected at all.

In addition, there are reports stating that a BP having amino group has a local irritative property (*Lancet*, 348, No. 9023, 345–346 (1996); *Br. Med. J.*, 295, No. 6609, 1301–1305 (1987)), that is, it is completely unclear whether or not the treatment of periodontitis by topical administration of BP to periodontal tissues or adjacent tissues thereof in human is actually possible.

Great concern has been directed toward the creation of a topical administration medicament useful as a periodontitis treating agent containing BP as the active ingredient, which has an alveolar bone-selective bone resorption inhibitory action, is convenient as the administration method and has high practical values clinically in human.

DISCLOSURE OF THE INVENTION

The present inventors have carried out examinations on the periodontitis treating agents for topical administration using a canine periodontitis model having periodontal tissues bearing resemblance to those of human, making use of incadronate whose periodontitis treating action had been confirmed by oral administration, and found unexpectedly that BP can be transferred alveolar bone-selectively and good alveolar bone resorption inhibitory action and periodontitis treating action can be expressed, when BP is topically injected using an alveolar mucosa injection method conventionally used as a method for injecting anesthetic drugs in the field of dentistry, thereby accomplishing the invention. What is more, this administration method was a topical administration method, which is easy to handle, has less burden to patients and has clinically high practical value.

Accordingly, the invention relates to a pharmaceutical composition for treating human periodontitis, which comprises a bisphosphonic acid derivative or a salt thereof and a pharmaceutically acceptable carrier, characterized in that it is for topical injection by an alveolar mucosa injection method. The injecting volume of the pharmaceutical composition of the invention for topical injection by an alveolar mucosa injection method is preferably from 100 to 300 μl per one administrating site. Also, a pharmaceutical composition in which the bisphosphonic acid derivative or a salt thereof is incadronic acid or a salt thereof is desirable, and a pharmaceutical composition in which concentration of incadronic acid or a salt thereof is from 3.33 to 100 μg/ml is more desirable. Dose of incadronic acid or a salt thereof is preferable from 0.5 μg to 15 μg per one administrating site.

In addition, according to the inventors' studies, canine periodontal tissues were apt to undergo influence of local irritation by BP, and good therapeutic effects could not be obtained due to the local irritation at a concentration of topical dose capable of achieving an alveolar bone concentration similar to the alveolar bone concentration at the time of systemic administration, so that it was considered that topical administration of a periodontitis treating agent containing BP to periodontal tissues in human, whose periodontal tissues are similar to those of canines, will be difficult due to this local irritation.

However, when the inventors have carried out further examinations, it was found unexpectedly that good alveolar bone resorption inhibitory action can be expressed by topically injecting incadronate into periodontal tissues in an amount far smaller than the dose predicted from the alveolar bone concentration at the time of systemic administration.

Accordingly, another embodiment of the invention is a pharmaceutical composition for treating periodontitis as a composition for human periodontal tissue topical injection, which comprises a bisphosphonic acid derivative or a salt thereof in an amount small enough so that local irritation to human periodontal tissues as the administration site can be accepted but the amount sufficient for exerting alveolar bone resorption inhibitory action by topical injection, illustratively, from 3.33 to 100 μg/ml of incadronic acid or a salt thereof and a pharmaceutically acceptable carrier.

In addition, the invention also relates to a dental cartridge that comprises the pharmaceutical composition of the invention.

Also preferred as other embodiments of the invention are a method for treating patients with periodontitis, characterized in that an effective amount of a bisphosphonic acid derivative or a salt thereof is administered by an alveolar mucosa injection method, a method for treating patients with periodontitis, characterized in that an injection comprising incadronic acid or a salt thereof in a concentration of from 3.33 to 100 μg/ml is topically administered to periodontal tissues of the patient in a volume of from 100 to 300 μl per one administration site, and use of a bisphosphonic acid derivative or a salt thereof for the manufacture of an agent for inhibiting alveolar bone resorption and for use in topical injection by an alveolar mucosa injection method.

The following describes the invention in detail.

The term "bisphosphonic acid derivative or a salt thereof" as used herein means a compound or a salt thereof which is characterized in that it is a structural analog to pyrophosphoric acid stable in the living body, has two phosphonic acid residues and has a bone resorption inhibitory action. Examples of the bisphosphonic acid derivatives already known as bone resorption inhibitors include clodronate, tiludronate, neridronate, pamidronate, incadronate, alendronate, olpadronate, EB-1053, risedronate, ibandronate, zoledronate, YM529 (1-hydroxy-2-(imidazo[1,2-a]pyridin-3-yl)ethane-1,1-bisphosphonic acid) and salts thereof. Preferred are incadronate, alendronate, olpadronate, EB-1053, risedronate, ibandronate, zoledronate and YM529, and particularly preferred is incadronate.

The "incadronic acid or a salt thereof" of the invention is a compound selected from incadronic acid and pharmaceutically acceptable salts thereof including incadronate (incadronate disodium). Hydrates, solvates and polymorphic substances thereof are also included therein. Preferred is incadronate.

The inventors studied practical administration methods that can transfer BP alveolar bone-selectively using incadronate. Administration methods generally employed for periodontitis treating agents, such as attachment and adhesion to gingiva, and administration into periodontal pockets, are poor in practical values because of the low transfer late of BP to alveolar bone and a possibility of causing gingival irritation. Furthermore the administration into periodontal pockets has further low transfer late due to a distance from the alveolar bone and has a possibility of causing leaking of a drug from the pockets into the mouth.

The inventors have found that topical injection into periodontal tissues around alveolar bone, namely into gingiva, alveolar mucosa, sublingual mucosa, palate part and the like, is most desirable as a method for transferring a drug to the alveolar bone. However, since the periodontal tissue around the alveolar bone where topical injection of a drug can be actually carried out is very small, the volume that can be administered is limited, and there is a possibility of causing patients a pain, so that further improvement of the administration method is desired.

Thus, the inventors have found that the use of an alveolar mucosa injection method which had not been used in the field of dentistry other than the infiltration anesthesia renders possible easy topical injection of a BP-containing periodontitis treating agent in a volume of from 100 to 300 μl per one site around the alveolar bone, and it also renders possible alveolar bone-selective transfer of effective amount of BP as will be described later so that good alveolar bone resorption inhibitory effect or periodontitis treating effect can be obtained by simple handling and with less burden to patients. That is, it was found for the first time in the world that the alveolar mucosa injection method is a method having high practical values for topically administrating a BP-containing periodontitis treating agent into human periodontal tissues.

The term "alveolar mucosa injection method" as used herein means a method in which a drug solution is injected between periosteum of the alveolar bone and alveolar mucosa by inserting a needle not vertically but in a laying position into a flexible oral mucosa region adjacent to gingiva (the alveolar mucosa shown in FIG. 1, or sublingual mucosa), preferably around a border with gingiva. Illustratively, a drug solution is injected by laying a needle into the alveolar mucosa shown in FIG. 1, preferably around the mucogingival junction when the injection is carried out on the buccal side of teeth, and into the sublingual mucosa, preferably a region close to the jaw bone, on the lingual side. Regarding the angle for inserting a needle, close to horizontal within a possible range is advantageous, because it hardly gives a pain to patients and the drug solution can be easily injected. Preferably, it may be inserted at a laying angle of 10 degrees or less based on the mucosa region. However, since the palate side of the upper jaw has no alveolar mucosa or a flexible mucosa analogous thereto, a drug is injected by inserting a needle into a region about 1 cm-distant from the tooth jaw region, and this method is also included in the invention as an embodiment of the alveolar mucosa injection method.

This alveolar mucosa injection method is also called a horizontal method or a sub-mucous injection method, which is a known injection method conventionally used as one of the infiltration anesthesia methods used in the field of dentistry. Since an anesthetic drug is injected not into gingiva but under a flexible alveolar mucosa such as a region between gingiva and cheek, this method is markedly simple, requires a short period of time and causes pain only at the first insertion, so that it is known as a method having less burden on the dentists in charge and patients (Periodontal Therapy (2nd edition), pp. 325–326 (1992), published by Ishiyaku Shuppan). The injection method called alveolar mucosa injection method, horizontal method or sub-mucous injection method conventionally used as one of the infiltration anesthesia methods is a preferred embodiment of the "alveolar mucosa injection method" of the invention.

Since desirable handling method of the alveolar mucosa injection method is disclosed in Periodontal Therapy (2nd edition), pp. 325–326 (1992), published by Ishiyaku Shuppan, its description is extracted in the following though the alveolar mucosa injection method of the invention is not restricted by this description.

"In carrying out, the vestibule of mouth is firstly exposed by pressing a lip or cheek with a finger or dental mirror, and a needle is inserted into a flexible mucosa having loose connective tissue (alveolar mucosa) only a few mm by laying it not vertically but horizontally. Thereafter, when a blister is formed under the mucosa by gradually starting release of the liquid and then the release is further continued toward distal side by laying the needle as such, a bank-like swelling is formed. (Omission) On the lingual side, similar swelling is formed by inserting it into a region of the sublingual mucosa close to the jaw bone. In this connection, since the palate side of the upper jaw does not have a flexible mucosa, usual infiltration anesthesia is carried out at 1 cm intervals on a region about 1 cm-distant from the tooth jaw."

The inventors have confirmed previously that oral administration of incadronate shows an alveolar bone resorption inhibitory action dose-dependently in a canine periodontitis model, and found that its suitable dose is 1.0 mg/kg (*J. Periodont. Res.*, 33, 196–204 (1998)). Thereafter, it was confirmed that the drug concentration in the alveolar bone is about 4 $\mu$g/g in that case.

It was found also that, by 10 or 100 $\mu$g/50 $\mu$l/kg (200 or 2,000 $\mu$g/ml drug concentration) of incadronate intragingival (substantially around gingiva) administration in a tooth movement model in rat, no effect is observed in the 10 $\mu$g/50 $\mu$l/kg group (average concentration in the alveolar bone: 0.6 $\mu$g/g), good tooth relapse inhibitory action is observed in the 100 $\mu$g/50 $\mu$l/kg group (average concentration in the alveolar bone: 14 $\mu$l/g), and local irritation is not observed in gross observation.

Contrary to the above knowledge, however, in a study using a canine model having periodontal tissues analogous to those of human, as will be shown later in the study example, it was unable to exert alveolar bone resorption inhibitory action by a periodontal tissue topical injection of 50 $\mu$g or 150 $\mu$l/150 $\mu$l/site (site: per one administration site; 333 or 1,000 $\mu$l/ml drug concentration) which gives an intra-alveolar bone drug concentration similar to the case of oral administration. What is more, a considerable local irritation was observed in the 150 $\mu$g/150 $\mu$l/site group, and it was considered that this was originated from the local irritative effect of incadronate. Actually, since the periodontal tissue is very small so that the injectable volume of a drug is limited, it was considered that it is difficult to achieve the above effective intra-alveolar bone drug concentration by an injection of a low drug concentration without local irritation.

The inventors have conducted intensive studies and unexpectedly found as a result that good alveolar bone resorption inhibitory action can be exerted when incadronate is topically injected by the alveolar mucosa injection method at a dose far smaller than the amount that can achieve the aforementioned intra-alveolar bone concentration at the time of oral administration. That is, it was found that a BP concentration having both of clinically acceptable low local irritative property and sufficient alveolar bone resorption inhibitory action is present (from 0.5 to 15 $\mu$g/150 $\mu$l in the case of incadronate, namely from 3.33 to 100 $\mu$g/ml as the drug concentration). This optimum BP concentration can be found also on other BPs than incadronate by confirming local irritation and alveolar bone resorption inhibitory action through topical BP injection studies, preferably topical injection studies by the alveolar mucosa injection method, using an animal model of a canine, monkey or the like having periodontal tissues analogous to those of human. In this regard, administration frequency and administration interval are concerned in the expression of local irritation property so that they should be taken into consideration optionally.

In the case of incadronate as one of the preferred embodiments of the invention, a drug concentration of from 3.33 to 100 $\mu$g/ml, more preferably from 10 to 80 $\mu$g/ml, most preferably from 25 to 75 $\mu$l/ml, is the optimum concentration having a clinically acceptable low local irritative property and sufficient alveolar bone resorption inhibitory action by topical injection, and incadronate of this concentration can be topically injected at a volume of from 100 to 300 $\mu$l, preferably from 150 to 200 $\mu$l, per one administration site. It is desirable that the administration is carried out to either the buccal side or lingual side, preferably both sides (two sites), per one tooth to be treated. This is administered once, or 2 to 10 times at intervals of 1 day to several weeks. Preferably, it is desirable to carry out the administration 2 to 10 times at intervals of 3 days to 14 days. More preferable dosage schedule should be optionally selected in response to the drug concentration, and it is desirable to narrow the administration intervals and increase the frequency in the case of a low concentration or to prolong the administration intervals and reduce the frequency in the case of a high concentration. For example, it is desirable to carry out the administration 3 to 9 times at one week intervals when 1.5 $\mu$g/150 $\mu$l–200 $\mu$l/site is administered to two sites per one tooth to be treated, 3 to 6 times at one week intervals when 5 $\mu$l/150 $\mu$l–200 $\mu$l/site is administered to two sites per one tooth to be treated, or 2 to 3 times at two week intervals when 15 $\mu$g/150 $\mu$l–200 $\mu$l/site is administered to two sites per one tooth to be treated.

The aforementioned alveolar mucosa injection method is suitable as the topical injection method, but even in the case of the use of other periodontal tissue injection methods such as an inter-dental papilla injection method, the efficacy at these concentrations can be expressed with the proviso that the method can perform injection at a volume of from 100 to 300 $\mu$l per one administration site. Accordingly, these injection methods are also included in the topical injection of the invention.

The alveolar bone resorption inhibitor for topical injection of the invention contains aseptic aqueous or non-aqueous solutions, suspending agents and emulsifying agents. Examples of the aqueous solutions include distilled water for injection and physiological saline. Examples of the non-aqueous solutions include propylene glycol, polyethylene glycol, plant oils such as olive oil, alcohols such as ethanol and Polysorbate 80 and the like. Such compositions may further contain auxiliary agents such as an antiseptic agent, a moistening agent, an emulsifying agent, a dispersing agent, a stabilizing agent, a solubilization-assisting agent and an isotonicity agent (e.g., xylitol, mannitol, sorbitol or ethylene glycol). They may be sterilized by filtration through a bacteria-retaining filter, blending of a germicide or irradiation, or produced under an aseptic condition. They can also be used by firstly producing aseptic solid compositions and then dissolving in sterile water or a sterile solvent for injection prior to use. From the viewpoint of clinical use, it is desirable to provide the alveolar bone resorption inhibitor of the invention particularly as a dental cartridge.

BEST MODE FOR CARRYING OUT THE INVENTION

Figure 1:
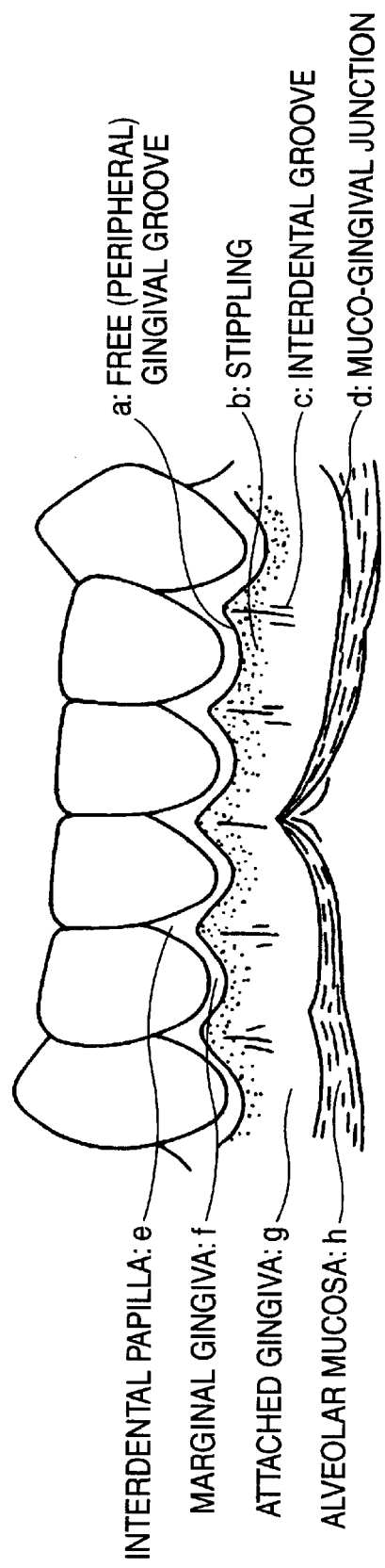
FIG. 1 shows a schematic view of tissues around gingiva.

The following examples show effects of the pharmaceutical composition of the invention for periodontitis treatment and formulations. In this connection, the scope of the invention is not restricted by the following examples.

EXAMPLE 1

Canine Periodontitis Model Study (Methods)

A total of 30 animals of female beagle dogs (1 to 2 years, body weight at the time of grouping 7.9 to 13.7 kg) were fed with a soft diet prepared by impregnating Gains Packen (AGF) with water from the previous day of ligation and used in this study. Under anesthesia with xylazine hydrochloride (Bayer) and pentobarbital, gingiva between second premolar (hereinafter, P2)/third premolar (hereinafter, P3), between P3/fourth premolar (hereinafter, P4) and between P4/first molar (hereinafter, M1) of right and left mandibles were incised with a surgical knife, and periodontal pockets were prepared around P3 and P4 using a periosteal elevator. An experimental periodontitis was induced by placing double-ligation of silk threads (surgical thread; Nescosuture (3-0), Morita) around the cervices of P3 and P4. In this case, reference points were prepared on the buccal side and lingual side of the crown of P4 at the height of gingival margin using dental drill. Since periodontal local conditions (dental calculus adhering state and periodontal condition) were almost uniform, scaling and brushing were not carried out, and the animals were divided into the following five groups by general conditions (body weight and age). 1) Control group: physiological saline, 2) incadronate 0.5 $\mu$l/site group, 3) incadronate 1.5 $\mu$g/site group, 4) incadronate 5.0 $\mu$g/site group and 5) incadronate 15 $\mu$g/site group.

The administration was started just after the surgical operation in each group. Incadronate (an injection, mfd. by Yamanouchi Pharmaceutical Co., Ltd.) was prepared and diluted with saline such that the administration liquid volume became 150 $\mu$l/site. The administration was carried out a total of three times, namely just after the ligation and 1 and 2 weeks after the ligation. The administration was carried out by the alveolar mucosa injection method using a 27 G injection needle attached to a glass micro-syringe. The injection needle was inserted horizontally to the alveolar mucosa close to the boundary between the alveolar mucosa and gingiva (muco-gingival junction) around the ligated tooth, and 150 $\mu$l of a drug solution was injected between periosteum of the alveolar bone and alveolar mucosa. The administration was carried out on both of the buccal and lingual side (a total of 4 sites per 1 mandible, 600 $\mu$l in total). Each animal was sacrificed by exsanguination 13 weeks after the final administration, and the mandibles including P3 and P4 of right and left side and the ribs were harvested and submitted to the intra-bone drug concentration measurement.

(Evaluation of alveolar bone loss inhibitory effect by standardized X-ray photographing)

The standardized X-ray photographing method (*J. Periodontol.*, 33, 164–171 (1962)) was employed, in which irradiation direction of X-ray to a subject and position of the film are always kept constant so that X-ray photographs of the same region of the same individual can be obtained repeatedly always under the same conditions. This time, in order to evaluate alveolar bone loss around P3 and P4 of right and left mandibles, a cap was formed between incisor tooth and M1 of both mandibles using an acrylic resin, and a fixing device was prepared by combining this cap with a film holder.

Each animal was anesthetized with xylazine hydrochloride and ketamine hydrochloride (Ketalar, Sankyo), and a dental film (Ultra Speed DF58, Kodak) was attached to the film holder on the fixing device to photograph X-ray by a dental X-ray photographing apparatus (Super Max 70, type HD-1, Morita Seisakusho).

Figure 2:
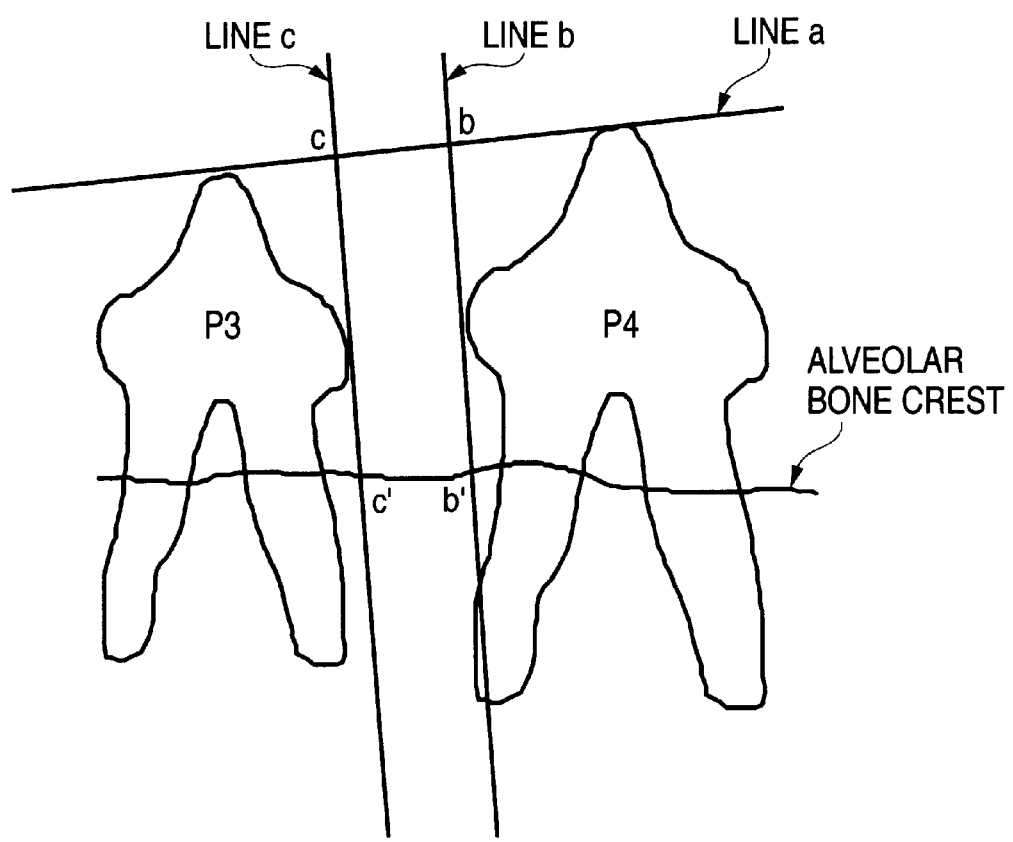
FIG. 2 shows the evaluation method of alveolar bone crest height, in Example 1. Symbols in this drawing have the following meanings. Line a: a line linking crests of tooth crowns of P4 and P3, line b and line c: perpendicular lines against line a passing the most mesial side of P4 tooth crown and the most distal side of P3 tooth crown, b and c: intersecting points (reference points) of line a with line b and line c, and b' and c': intersecting points of alveolar bone crest with line b and line c.

In this case, height of the alveolar bone crest was measured using the evaluation method shown in FIG. 2. That is, an X-ray film was measured under a stereoscopic microscope (objective×1, eyepiece×10), an OHP sheet was put on the X-ray film, and line a, line b and line c were marked on the OHP sheet using a ceramic knife, thereby obtaining respective two points b and b' and c and c' on line b and line c. Distances between the b-b' and c-c' were respectively defined as the distances from the reference points (b and c points) to the alveolar bone crest. The length of alveolar bone loss was expressed by averaging values obtained by subtracting the sum of b-b' and c-c' distances in each individual at the time of each week from the sum of b-b' and c-c' distances at the time of ligation.

(Measurement of clinical Scores)

(1) Depth of Pocket (Probing Depth; PD)

Measurement of the depth of periodontal pockets was carried out by a four point measuring method in accordance with *J. Clin. Periodontol.*, 4, 173–190 (1997)).

(2) Gingival Recession

Regarding the length of gingival recession, the distance from the reference point on the tooth crown prepared at the time of ligation to the gingival margin was measured on two regions, the buccal and lingual side, of P4 at the time of each week in each individual, and expressed as the average value.

(3) Attachment Level (AL)

Attachment level is an index for measuring position of the bottom of gingival sulcus (pocket bottom), and was expressed as the distance from the pocket bottom to the reference point on the tooth crown. That is, a value of the depth of pocket plus the length of gingival recession was used as the attachment level.

(4) Gingival Index (GI)

Regions of inflammation and degree of the symptoms of gingiva were evaluated in accordance with J. Periodontol., 38, 602–610 (1967)).

(Measurement of Intra-alveolar Bone Drug Concentration and Intra-rib Drug Concentration)

Root of the left fourth premolar was extracted using cutting pliers, the whole mandible containing jaw bone and alveolar bone was divided up and down into two, and the upper ½ was considered as the alveolar bone. Also, the intra-rib drug concentration was measured using the epiphyseal region of the rib that had been frozen at $-40°$ C. after anatomy. Incadronate was extracted from these samples using a calcium precipitation method and its intra-bone drug concentration was measured by an HPLC method.

(Results)

Respective data were calculated as separate values of right and left teeth. SAS (EXSAS-ATAT) was used in the all statistical analyses.

Figure 3:
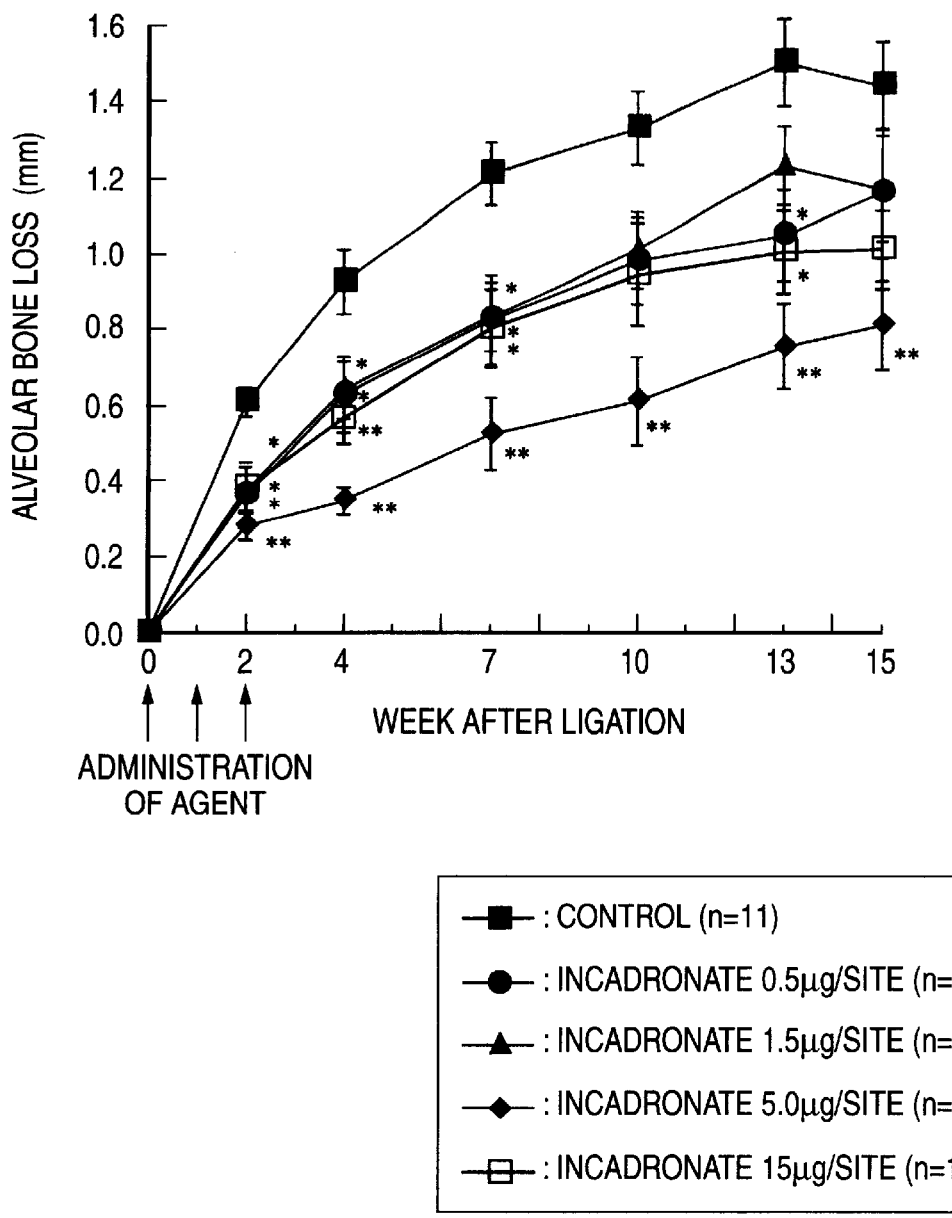
FIG. 3 is a graph showing the effect of incadronate on alveolar bone loss, in Example 1. The drawing shows average value±standard error of mean of the length of alveolar bone loss after ligature placing with the passage of time. Parentheses in the explanatory notes indicate the number of samples in each group. The symbols * and ** show significant differences against the control group (* $p<0.05$, ** $p<0.01$, Dunnett's multiple comparison test).

A result of the alveolar bone loss inhibitory action is shown in FIG. 3. Almost periodical loss of alveolar bone was found in the control group after ligation, and this was inhibited in the incadronate-treated groups and its action was most potent at a dose of 5 $\mu$g/site.

Also, aggravation of the clinical scores of periodontitis was inhibited in the incadronate-treated groups. The clinical scores were as follows.

(1) Depth of Pocket

A transient acceleration of pocket depth with its peak 2 weeks after the ligation was observed in the control group. Incadronate significantly inhibited acceleration of pocket depth 2 and 4 weeks after the ligation at a dose of 1.5 $\mu$g/site or more.

(2) Gingival Recession

Acceleration of gingival recession by ligation was observed with the passage of time in the control group. Incadronate significantly inhibited acceleration of gingival recession in and after 4 weeks of the ligation at a dose of 5 $\mu$l/site or more, and significantly inhibited only after 15 weeks of the ligation at a dose of 1.5 $\mu$l/site.

(3) Attachment Level

Reduction of attachment level by the ligation was observed almost periodically in the control group. Incadronate significantly inhibited reduction of attachment level in and after 2 weeks of the ligation at a dose of 5 $\mu$l/site or more, and significantly inhibited after 4 and 15 weeks of the ligation at a dose of 1.5 $\mu$l/site.

(4) Gingival Index (GI)

A transient exacerbation of gingival index was observed with its peak 2 weeks after the ligation in the control group. Incadronate significantly inhibited this exacerbation of gingival index after 2 weeks of the ligation at a dose of 1.5 $\mu$g/site or more.

(Intra-alveolar Bone Drug Concentration and Intra-rib Drug Concentration)

The results are shown in Table 1. In the 5 to 15 $\mu$g/site-administered groups, intra-rib concentration of incadronate was about ¹⁄₁₀ of the intra-alveolar bone concentration, thus confirming that the injections of the invention can achieve alveolar bone-selective transfer of BP.

TABLE 1

| Dose ($\mu$g/site) | The number of cases | Intra-alveolar bone drug concentration ($\mu$g/g bone) | Intra-rib drug concentration ($\mu$g/g bone) |
|---|---|---|---|
| 0.5 | 6 | 0.058 ± 0.008 | N.D. |
| 1.5 | 6 | 0.174 ± 0.011 | N.D. |
| 5 | 5 | 0.356 ± 0.070 | 0.033 ± 0.003 |
| 15 | 6 | 1.035 ± 0.313 | 0.091 ± 0.016 |

N.D. indicates detection limit (0.025 $\mu$g/g) or less.

COMPARATIVE EXAMPLE 1

High Dose Topical Administration Study in Canine Periodontitis Model (Methods)

Using 26 animals of beagle dog (3 to 6 years, body weight at the time of grouping 6.1 to 12.9 kg), topical administration study in a canine periodontitis model were carried out on a), control group: physiological saline, b) incadronate 50 $\mu$l/site group and c) incadronate 150 $\mu$g/site group. The study was carried out in the same manner as in Example 1, except that the administration was carried out a total of three times, namely just after ligation and 2 and 4 weeks after the ligation, and the mandibles and ribs were collected 8 weeks after the final administration and submitted to the intra-bone drug concentration measurement.

(Results)

Both of the alveolar bone loss inhibitory action and clinical scores showed no significant difference between the control and incadronate-treated groups. Intra-alveolar bone concentration of incadronate was 5.67 and 4.28 $\mu$g/g bone. This was similar to the intra-alveolar bone drug concentration of about 4 $\mu$g/g at the time of the completion of 26 weeks oral administration of 1.0 mg/kg of incadronate (J. Periodont. Res., 33, 196–204 (1998)).

In addition, when local irritation to the lamina propria mucosae of the administered sites was observed, a) slight mononuclear cell infiltration was observed partly in the control group, and b) slight mononuclear cell infiltration was also observed partly in the incadronate 50 $\mu$g/site group, and its relative frequency and degree were higher than those in the control group. On the other hand, c) in the incadronate 150 $\mu$g/site group, bleeding, fibrin precipitation, inflammatory cell infiltration, salivary gland and muscular tissue damage were observed in all cases one week after the final administration, and considerable tissue damages such as those accompanied by an ulcer of a part of gingival mucosa were observed.

By the topical injection capable of giving an intra-alveolar bone drug concentration similar to the level by the conventional oral administration, both of the action to inhibit alveolar bone loss and the action to inhibit aggravation of clinical scores of periodontitis were not found. Also, since inflammation was observed on the administered sites, it was considered a possibility that this topical inflammation induces bone resorption and it was suggested a possibility that this topical inflammation compensates the alveolar bone resorption inhibitory action of incadronate.

EXAMPLE 2

FORMULATION EXAMPLES

Formulation Example 1

A 3.3, 10.0, 33.3 or 100 μg portion of incadronate was dissolved in saline and adjusted to 1 ml, and this was packed in a one ml capacity cartridge to obtain a dental cartridge containing the pharmaceutical composition of the invention.

Formulation Example 2

A 3.3, 10.0, 33.3 or 100 μg portion of incadronate and either of 42.6 mg of xylitol, 51 mg of mannitol, 51 mg of sorbitol or 21 mg of glycine hydrochloride as a isotonicity agent were dissolved in saline and adjusted to 1 ml. By packing this in a one ml capacity cartridge, a dental cartridge containing the pharmaceutical composition of the invention was obtained.

Formulation Example 3

A 7.5, 25 or 75 μg portion of incadronate and either of 42.6 mg of xylitol, 51 mg of mannitol, 51 mg of sorbitol or 21 mg of glycine hydrochloride as an isotonicity agent were dissolved in physiological saline and adjusted to 1 ml. By packing this in a one ml capacity cartridge, a dental cartridge containing the pharmaceutical composition of the invention was obtained.

Industrial Applicability

The pharmaceutical composition for periodontitis treatment of the invention, which comprises a bisphosphonic acid derivative or a salt thereof and a pharmaceutically acceptable carrier, is useful as a periodontitis treating agent having less systemic side effects, because BP is transferred alveolar bone-selectively by its topical injection using the alveolar mucosa injection method instead of the conventional systemic administration.

Accordingly, it efficiently inhibits alveolar bone resorption accompanied by periodontitis, controls recession of alveolar bone crest and alveolar bone density which are generated accompanied by alveolar bone resorption and prevents aggravation of clinical scores of periodontitis such as gingivitis, bleeding, depth of periodontal pockets, reduction of attachment level and the like.

In addition, the pharmaceutical composition for periodontitis treatment, as a composition for use in the human alveolar tissue topical injection, which comprises incadronic acid or a salt thereof in a concentration of from 3.33 to 100 μg/ml and a pharmaceutically acceptable carrier, has low local irritative property and good alveolar bone resorption inhibitory action and therefore is useful as a BP-containing pharmaceutical composition for periodontitis treatment which enabled its topical administration to alveolar tissues (e.g., alveolar mucosa and the like) for the first time.

What is claimed is:

1. A method for treating periodontitis of a patient, characterized in that an effective amount of a bisphosphonic acid derivative or a salt thereof is administered by an alveolar mucosa injection method.

2. A method for treating periodontitis of a patient, characterized in that an injection comprising incadronic acid or a salt thereof in a concentration of from 3.33 to 100 μg/ml is topically administered to periodontal tissues of the patient in a volume of from 100 to 300 μl per one administration site.

3. The method according to claim 1, wherein the injection volume per one administration site is from 100 to 300 μl.

4. The method according to claim 1, wherein the bisphosphonic acid derivative or a salt thereof is incadronic acid or a salt thereof.

5. The method according to claim 4, wherein incadronic acid or a salt thereof has a concentration of from 3.33 to 100 μg/ml.

6. The method according to claim 5, wherein the incadronic acid or a salt thereof is incadronate disodium.

7. A dental cartridge, which comprises a pharmaceutical composition comprising bisphosphonic acid or a salt thereof in a concentration of from 3.33 to 100 μg/ml.

* * * * *